United States Patent
Heil et al.

(10) Patent No.: US 6,422,071 B1
(45) Date of Patent: Jul. 23, 2002

(54) STONE PECKING MACHINE

(75) Inventors: Phillip J. Heil, Harrow; Benjamin William Dollar, Windsor, both of (CA)

(73) Assignee: Ventra Group, Inc., Rochester Hills, MI (US)

( * ) Notice: Subject to any disclaimer, the term of this patent is extended or adjusted under 35 U.S.C. 154(b) by 0 days.

(21) Appl. No.: 09/769,592

(22) Filed: Jan. 25, 2001

(51) Int. Cl.[7] .............................................. G01B 21/30
(52) U.S. Cl. ........................................ 73/150 R; 73/7
(58) Field of Search ........................... 73/7, 12.01, 117, 73/117.1, 150 R, 432.1, 865.8

(56) References Cited

FOREIGN PATENT DOCUMENTS

| DK | 3816229 C | * | 6/1989 | .......... G01M/17/00 |
|---|---|---|---|---|
| JP | 09-061303 | * | 3/1997 | ........ G01M/17/007 |
| WO | WO 99/39179 | * | 8/1999 | ............ G01N/3/56 |

* cited by examiner

Primary Examiner—Hezron Williams
Assistant Examiner—Rodney Frank
(74) Attorney, Agent, or Firm—Dykema Gossett PLLC

(57) ABSTRACT

A stone pecking damage analyzer is provided which includes an enclosure frame. A pivotal first conveyor wheel is also provided. Spaced from the fixed conveyor wheel is a second conveyor wheel. A conveyor belt is fitted upon the two conveyor wheels. An automotive tire/wheel combination is mounted for rotation in contact with the conveyor belt planar surface. A variable speed motor torsionally coupled to the shaft powers the tire/wheel combination. A tubular conduit delivers stones to the conveyor's planar surface. An aggravator manipulates the tubular conduit to increase the delivery of stones to the conveyor. A deflector is also provided for redirecting stones delivered to the tire by the conveyor and thereafter accelerated by the tire. A mounting system hangs an automotive vehicle coated body panel in a position commensurate to its position with respect to the vehicle wheel well.

8 Claims, 2 Drawing Sheets

STONE PECKING MACHINE

FIELD OF THE INVENTION

The present invention relates to a machine to empirically analyze the effect of the impact of foreign objects from a road upon the coating on body panels of an automotive vehicle. More particularly, the present invention relates to a machine which is used to empirically analyze the effect of stone pecking damage on an automotive vehicle providing accelerated results and simulating such damage in a manner more akin to that which actually occurs during vehicle operation.

BACKGROUND OF THE INVENTION

When an automotive vehicle is moving at a high speed, collisions of small stones or the like against paint coated surfaces of body panels adjacent the wheel wells are unavoidable. There are cases where such impacts from small stones and other foreign particles against the body panels form cracks in the paint or peel off the paint. Such damage is often called paint chipping. If the paint chipped body panel is exposed to water, ice or other precipitation, rust can form on the body panel. In many regions of the world such as the northern part of North America and the northern part of Europe where large quantities of rock salt and sand are scattered on roads to melt ice or add to the tractive value of the road pavement, it is particularly important that the paint on the portions of vehicle body panels close to the wheel wells be covered with a paint coating having a high degree of chip resistance.

The painting technique utilized for steel body panels of most automotive vehicles is a multiple step process wherein the body panel is first chemically treated with iron or zinc phosphate. An electro-deposited coating (i.e. primer), an intermediate base coat paint and a plurality of clear top coats are typically applied. In order to determine if such technique will provide a suitable coating which can withstand the normal impact with rocks or small objects, empirical testing is required.

Typically, the empirical testing is often performed by operating the vehicle over a special test track or an off-road test facility. Empirical testing at an off-road facility brings forth several disadvantages. One disadvantage is the time required to perform the test. To simulate real world conditions, the body panels on the test vehicle should be identical to those which will be placed on the production vehicle. Therefore, a long lead time must be provided between the road testing of new body styles and the production run of the body panel. Body styling is very important in the automotive industry and is sometimes the predominant factor of why a vehicle may or may not sell in the marketplace. It is desired that the actual body panel shape be kept secret. Accordingly, another disadvantage of road testing is the difficulty to conduct tests in real-world conditions and prevent new styling changes from being viewed by those who wish to destroy a manufacturer's commercial secrecy.

Machines have been developed to test the adhesion of paint coatings on steel sheet test plaques. However, many of these machines are primarily directed toward the effects of environmental conditions upon the paint and are not truly directed toward determining the amount and distribution of paint chipping which can occur by impingement of articles upon the vehicle. Another major disadvantage of many prior testing machines is that they do not properly simulate actual road conditions. In many machines, rocks were simply thrown at or dropped upon or scrubbed into painted surfaces. The location of the body panel with respect to its actual location on the automotive vehicle was not properly simulated. As mentioned previously, much of the paint chip damage on an automotive vehicle comes from small stones or particles which have been accelerated by the vehicle wheels after the vehicle has driven over them. Therefore, it is desirable that the machine not only simulate the speed of the particle, but the relative directional velocity of the particle with respect to the vehicle wheel which accelerates the particle.

It is desirable to provide an empirical testing machine which can simulate stone pecking and give accelerated results allowing such data to be quickly incorporated into the design of the painted body panels. It is also desirable to provide an empirical testing machine which closely simulates the actual road conditions that the painted body panel is exposed to.

SUMMARY OF THE INVENTION

To meet the above-noted desires, the revelation of the present invention is made manifest. In a preferred embodiment, the machine of the present invention brings forth the freedom of accelerated empirical testing of stone pecking on a paint coating of an automotive vehicle body panel. The machine of the present invention aids in the preservation of commercial security in the development of automotive panels by providing empirical stone pecking tests upon coated surfaces of body panels that closely simulate actual, real-world conditions. Additionally, the machine of the present invention provides feedback to the design of the panels before production tooling is constructed.

A preferred embodiment of the present invention includes an enclosure frame. A first conveyor wheel having a pivotal axis fixed with respect to the enclosure frame is also provided. Spaced from the fixed conveyor wheel is a second conveyor wheel which has a rotational axis fixed with respect to the enclosure frame. A conveyor belt is fitted upon the two conveyor wheels and provides a generally planar surface. A hub having a rotational axis generally vertically aligned with the second conveyor wheel is connected with a shaft. An automotive tire/wheel combination is mounted for rotation on the hub, with the tire being in contact with the conveyor belt planar surface. A variable speed motor torsionally coupled to the shaft powers the tire/wheel combination and the conveyor belt for rotation. A platform is provided which is pivotally mounted with respect to the enclosure. Connected on the platform is an electric motor which powers the shaft and is torsionally coupled with the tire/wheel combination and conveyor belt. A tubular conduit delivers stones to the conveyor's planar surface. An aggravator manipulates the tubular conduit to increase the delivery of stones to the conveyor. A deflector is also provided for redirecting stones delivered to the tire by the conveyor and thereafter accelerated by the tire. A mounting system hangs an automotive vehicle coated body panel in a position commensurate to its position with respect to the vehicle wheel well. A bin is provided for receiving those stones accelerated by the tire and impacted with the body panel. The bin has an opening at an elevation lower than the planar surface and the bin has a lower outlet. An auger is provided for delivering the stones from an outlet of the bin to the tubular conduit. An electric motor is provided to power the auger.

It is an object of the present invention to provide a machine which can empirically test stone pecking on painted automotive vehicle body panels.

It is an object of the present invention to provide a stone pecking testing machine which gives empirical results which closely approximate actual road conditions.

The above noted and other objects of the present invention will become apparent to those skilled in the art from a review of the invention as provided in the accompanying drawings and detailed description of the preferred embodiment.

DETAILED DESCRIPTION OF THE PREFERRED EMBODIMENT

Figure 1:
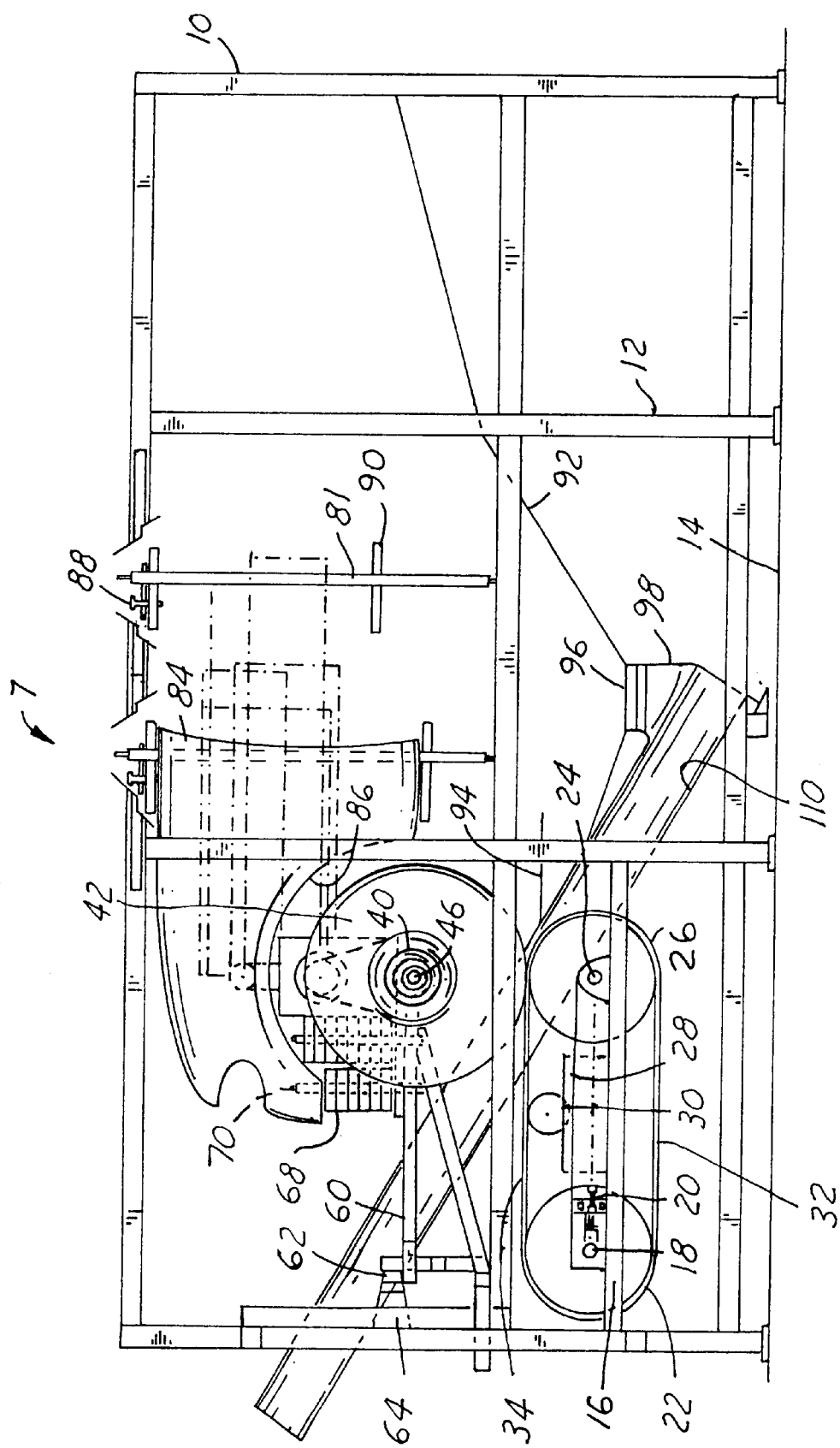
FIG. 1 is a side elevational view of a preferred embodiment stone pecking testing machine according to the present invention.
Figure 2:
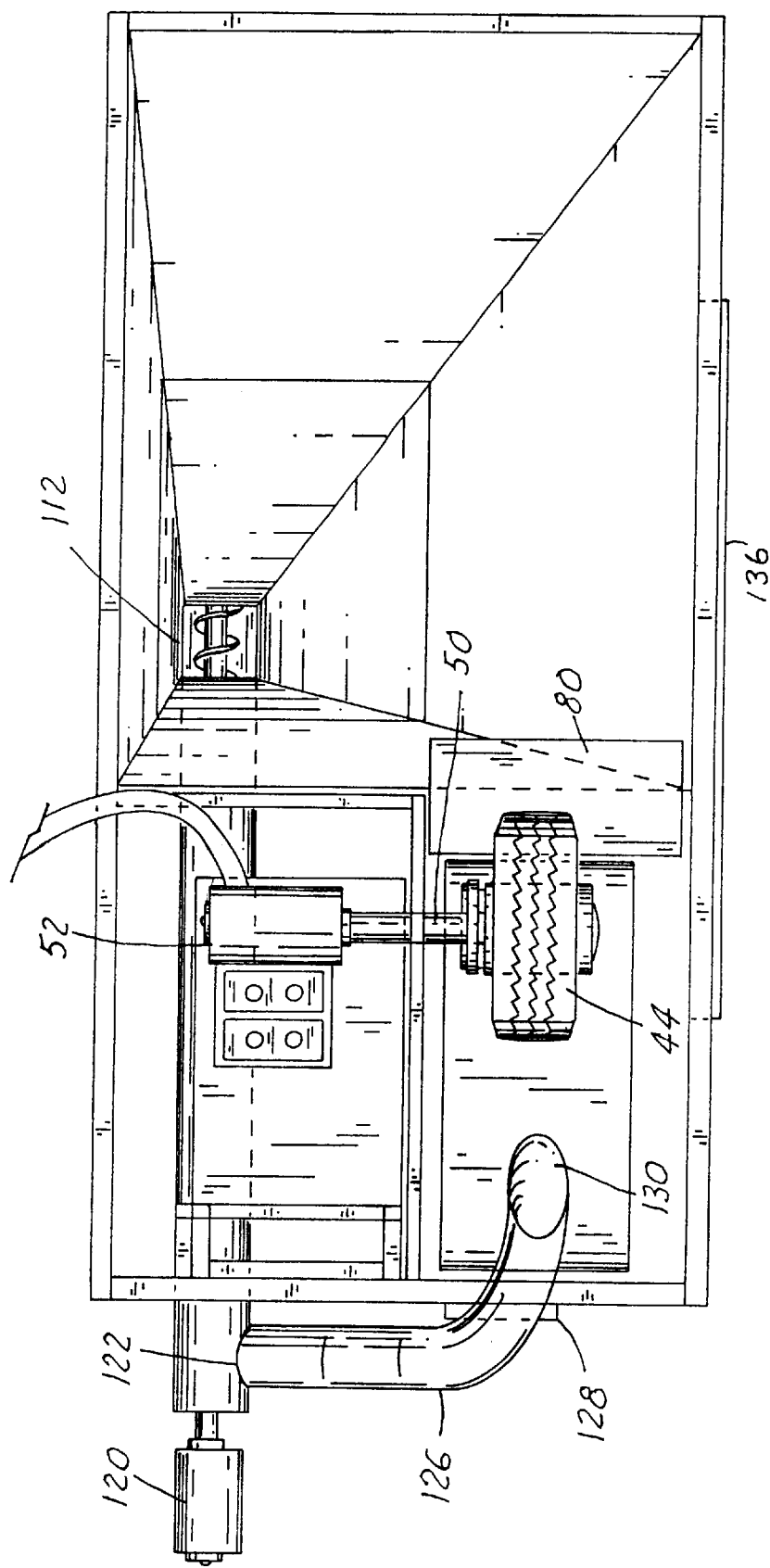
FIG. 2 is a top view of the stone pecking machine shown in FIG. 1.

Referring to FIGS. 1 and 2, the stone pecking empirical testing machine 7 of the present invention has an enclosure frame 10. The machine 7 can be utilized to empirically analyze the effects of stone peck damage upon a painted coating on an automotive vehicle body panel. The enclosure frame 10 includes a plurality of upright members 12 which are connected to a lower foundation 14. Connecting two of the upright members 12 toward a forward end of the machine 7 is a cross beam 16. The cross beam 16 has adjustably fixably connected thereto a first bearing block 18. Bearing block 18 can be adjusted generally fore and aft for changing a conveyor belt by an adjustment mechanism 20. The first bearing block 18 provides a horizontal rotational axis that is generally fixed with respect to the enclosure 10. The first conveyor belt wheel 22 has an 18 inch diameter.

Cross beam 16 also has fixably connected thereto and spaced away from the first bearing block 18, a second bearing block 24. The second bearing block 24 provides a generally horizontal rotational axis fixed with respect to the enclosure frame 10 for a second conveyor wheel 26. The conveyor wheels 22 and 26 have generally equal diameters. The cross beam 16 also supports a stand 28 which rotatably mounts an idler wheel 30. A belt 32 is fitted upon the first conveyor wheel 22 and the second conveyor wheel 26 and the idler wheel 30. The belt 32 has a top planar surface 34 which is in contact with the idler wheel 30. The belt 32 will typically be made from vulcanized rubber and will be 12 inches or centimeters wide.

The machine 7 is also provided with a rotative hub 40. The hub 40 is a universal-type hub which can be mounted to a small automotive wheel/tire combination such as on a sub-compact vehicle or a larger wheel/tire combination such as on a large sport utility vehicle or light truck. As shown in FIGS. 1 and 2, the hub 40 has mounted thereon a wheel 42 along with a connected tire 44. The hub 40 has a horizontal rotational axis 46 which is generally vertically aligned with the rotational axis of the second bearing block 24. The tire 44 is placed in contact with the top planar surface 34 adjacent the second conveyor wheel 26.

Torsionally coupled with the hub 40 is a shaft 50. The shaft 50 is powered for rotation by an electric motor 52. The motor 52 is an AC continuously variable speed motor. In the example shown the motor 52 is a 5.0 horsepower motor. The motor 52 can rotate the shaft 50 at 1,994 rpms. The motor 52 not only powers the hub 40 and wheel/tire combination 42, 44, but also powers the conveyor belt 32 by its contact with the tire 44.

The motor is connected on a platform 60. The platform 60 can move with respect to the enclosure pin by virtue of its pivotal connection 62 with a pivotal mount 64 which is fixably attached to the enclosure frame 10. As shown in FIG. 1, the platform 60 is angularly biased in a clockwise direction by a series of weights 68 held to the platform 60 by rods 70. The weights can be selected to simulate the effect of different weighted vehicles.

A steel deflector 80 is provided. The deflector 80 redirects stones delivered to the tire 44 by the conveyor belt 32 and then thereafter accelerated by the tire 44.

Vertical rails 81 are provided for hanging a painted automotive vehicle front fender panel 84 having a wheel well 86. The vertical rails can also hang quarter panels or doors. The rails 81 are connected on top by mounting fixture 88. The rails 81 also have positionally adjustable clamps 90 to hold the body panel in a position representative of its position with respect to a vehicle wheel in a real-world situation.

A bin 92 is also provided. The bin 92 has a top opening 94 which is at least partially lower than the top planar surface 34. The bin 92 has a lower outlet 96 which feeds into a sump 98. The sump 98 is intercepted by a slanted passageway 110. The slanted passageway 110 is tubular and contains an auger 112. The auger 112 is powered by a 2 hp electric motor 120. The slanted passage 110 has an outlet 122 which feeds into a lateral declining tubular conduit 126. The tubular conduit 126 is acted upon by an aggravator 128. The tubular conduit 126 also has an outlet 130. On operation a vehicle panel 84 representative of a front fender quarter panel (or other body panel part) is hung within the enclosure 10 on the rails 81 and is clamped into position with the clamps 90. A wheel with a tire is rotatively mounted to the hub 40. An appropriate amount of weight is placed upon the platform 60. This will cause the tire 44 to be loaded with a vertical force upon the top planar surface 34 and the second conveyor wheel 26.

The stones will be dumped into the bin 92. The auger 112 is rotated by the motor 120 and will typically deliver the stones into the tubular conduit 126. The aggravator 128 will vibrate the tubular conduit 126 to cause the stones to be more evenly distributed and the stones will be delivered to the planar surface 34 of the belt 32. The stones are typically accelerated by the tire to a velocity equivalent to actual road conditions whereon they will then impact the panel 84. A deflector plate 80 will direct the stones to the area of the panel to be evaluated. After the stones have impacted the panel, the stones will fall into the bin 92 and then slide down the slanted floor of the bin to the outlet 96 and to the sump 98 wherein they are again recycled by the auger 112. A dust collection system having fans and filters is utilized to collect the dust from inside the enclosure. An access door 136 having a plexiglass window is provided to allow visual inspection of the testing process.

The present inventive stone pecking empirical analyzing machine has been shown in a preferred embodiment. However, it would be apparent to those skilled in the art that various modifications can be made to the present invention from that as described in present specification and drawings without departing from the spirit or scope of the present invention as it is encompassed by the disclosure of the specification and drawings and by the following claims.

We claim:

1. A machine to empirically analyze the effect of stone peck damage upon a coating on an automotive vehicle body panel, said machine comprising;

an enclosure frame;

a first conveyor wheel having a rotational axis fixed with respect to said enclosure frame;

a second conveyor wheel having a rotational axis fixed with respect to said enclosure frame, said second conveyor wheel being spaced from said first conveyor wheel;

a belt fitted upon said conveyor wheels, said belt providing a generally planar surface;

a hub having a rotational axis generally vertically above said belt planar surface;

an automotive tire and wheel combination mounted for rotation on said hub, said tire being in contact with said belt generally planar surface;

a shaft connected with said hub;

a variable speed electric motor torsionally coupled to said shaft for rotating said tire and said conveyor;

a platform to support said motor, said platform being movable with respect to said enclosure frame;

weights for loading said platform to determine the force of contact between said tire and said belt of said planar surface;

a tubular conduit for delivering stones to said conveyor planar surface;

an aggravator for vibrating said tubular conduit to better distribute said stones delivered by said tubular conduit;

a deflector for redirecting stones delivered to said tire by said conveyor and then accelerated by said tire;

a mounting system for mounting an automotive vehicle coated body panel in a fixed position with respect to said tire and wheel;

a bin for receiving stones accelerated by said tire from impact with said body panel, said bin having an opening at an elevation lower than said planar surface of said belt and said bin having a lower outlet;

an auger for delivering said stones from said outlet to said tubular conduit; and an electric motor for powering said auger.

2. A machine to empirically analyze the effect of stone peck damage upon a coating on an automotive vehicle body panel as described in claim 1, wherein said second wheel has a diameter generally equal to a diameter of the first wheel, and said second wheel is horizontally aligned with respect to said first wheel.

3. A machine to empirically analyze the effect of stone peck damage upon a coating on an automotive vehicle body panel as described in claim 1, wherein there is additionally an idler wheel positioned intermediate said first and second wheel to support said planar surface of said belt.

4. A machine to empirically analyze the effect of stone peck damage upon a coating on an automotive vehicle body panel as described to claim 1, wherein the rotational axis of said second conveyor wheel and said hub are vertically aligned.

5. A machine to empirically analyze the effect of stone peck damage upon a coating on an automotive vehicle body panel as described in claim 1, wherein said platform is pivotally connected to said enclosure frame.

6. A machine to empirically analyze the effect of stone peck damage upon a coating of an automotive vehicle body panel as described in claim 1, wherein said motor which powers said shaft also powers said conveyor belt.

7. A machine to empirically analyze the effect of stone peck damage upon a coating of an automotive vehicle body panel as described in claim 1, wherein said enclosure has an exhaust system to collect dust generated by said machine.

8. A machine to empirically analyze the effect of stone peck damage upon a coating on an automotive vehicle body panel, said machine comprising:

an enclosure frame;

a first conveyor wheel having an axis fixed with respect to said enclosure frame;

a second conveyor wheel having a diameter generally equal to the diameter of said first conveyor wheel, said second conveyor wheel having a rotational axis fixed with respect to said enclosure frame, said second conveyor wheel being horizontally aligned and spaced from said first conveyor wheel;

a belt fitted upon said conveyor wheels, said belt providing a generally planar surface;

a universal hub having a rotational axis generally vertically above said belt planar surface, said hub rotational axis being vertically aligned with said second conveyor wheel rotational axis;

an automotive tire and wheel combination mounted for rotation on said hub, said tire being in contact with said belt generally planar surface;

a shaft connected with said hub;

a variable speed electric motor torsionally coupled to said shaft for rotating said tire and said conveyor;

a platform to support said motor, said platform being pivotally mounted with respect to said enclosure frame;

weights for loading said platform to determine the force of contact between said tire and said belt of said planar surface;

a tubular conduit for delivering stones to said conveyor planar surface;

an aggravator for vibrating said tubular conduit to better distribute said stones delivered by said tubular conduit;

a positionally adjustable deflector for redirecting stones delivered to said tire by said conveyor and then accelerated by said tire;

a mounting system for mounting an automotive vehicle coated body panel in a fixed position with respect to said enclosure;

a bin for receiving stones accelerated by said tire from impact with said body panel, said bin having an opening at an elevation lower than said planar surface of said belt and said bin having a lower outlet;

an auger for delivering said stones from said outlet to said tubular conduit; and an electric motor for powering said auger.

* * * * *